(12) United States Patent
Drevillon et al.

(10) Patent No.: US 6,657,708 B1
(45) Date of Patent: Dec. 2, 2003

(54) APPARATUS FOR OPTICALLY CHARACTERISING THIN LAYERED MATERIAL

(75) Inventors: Bernard Drevillon, Clamart (FR); Edouard da Silva, Lille (FR); Benferhat Ramdane, Oncy-Ecole (FR)

(73) Assignee: Jobin Yvon S.A., Longjumeau (FR)

( * ) Notice: Subject to any disclaimer, the term of this patent is extended or adjusted under 35 U.S.C. 154(b) by 0 days.

(21) Appl. No.: 09/807,581
(22) PCT Filed: Oct. 12, 1999
(86) PCT No.: PCT/FR99/02460
§ 371 (c)(1), (2), (4) Date: Sep. 25, 2001
(87) PCT Pub. No.: WO00/22416
PCT Pub. Date: Apr. 20, 2000

(30) Foreign Application Priority Data

Oct. 14, 1998 (FR) .............................. 98 12886

(51) Int. Cl.⁷ .............................................. G01N 21/00
(52) U.S. Cl. ........................... 356/73; 356/301; 356/369
(58) Field of Search ........................ 356/73, 301, 369, 356/72

(56) References Cited

FOREIGN PATENT DOCUMENTS

| EP | 0 508 257 A2 | 10/1992 | | |
|---|---|---|---|---|
| EP | 0 663 590 A1 | 7/1995 | | |
| JP | 09-213652 | * | 8/1997 | ......... H01L/21/268 |
| WO | WO 97/05473 | 2/1997 | | |

OTHER PUBLICATIONS

Watanabe et al., "Surface Analysis by Raman–Elliposometry Spectroscopy", May 1985, Journal of the Vacuum Society of Japan, vol. 28, No. 11, pp. 810–813.*

* cited by examiner

Primary Examiner—F. L. Evans
Assistant Examiner—Kara Geisel
(74) Attorney, Agent, or Firm—Arent Fox Kintner Plotkin & Kahn, PLLC

(57) ABSTRACT

The invention concerns an apparatus for optically characterising a thin-layer material by backscattering Raman spectometry comprising a frame, a monochromatic excitation laser source (21), optical means (23, 24) directing a light flux emitted by the source towards the material to be characterised, provided with means (22) homogenising the distribution of energy per surface unit, over a minimum surface of some tens of square micrometers, and means for collecting (24) and selecting (27, 28) the light diffused by Raman effect. The apparatus further comprises reflectometric measuring means (3–14) integral with the Raman measuring means, including reflectometric excitation means (3–9) directed on the same sample zone as the Raman excitation means.

13 Claims, 2 Drawing Sheets

APPARATUS FOR OPTICALLY CHARACTERISING THIN LAYERED MATERIAL

This invention relates to an apparatus for optically characterising thin layered material.

Such characterising that is non-destructive and can therefore be used in situ during manufacture or for checking finished products, enables knowing at least certain elements making up the analysed matter and possibly their concentration. It can also enable accessing the thickness of thin layers.

To perform characterising, we have known until now, on the one hand Raman spectroscopy devices, on the other hand reflectometers, photometers or ellipsometers, that may be spectroscopic.

We know that the Raman effect is caused by a sample lit at a given wavelength $\lambda_e$ diffusing a Raman luminous beam at a wavelength $\lambda_r$ close to $\lambda_e$ whose intensity is very small with respect to that of the Rayleigh light which is diffused at the same wavelength $\lambda_e$ as the lighting beam. In case when the Raman spectrometer is coupled with a microscope, the lighting beam is currently under a normal incidence with respect to the sample and the Raman diffusion is measured by its intensity and by its spectrum in a solid wide angle.

We also know reflectometry characterising. The purpose is then to light the sample under an angle that is often small (vastly different from the normal to the sample) and to analyse the light that is reflected specularly by the sample. We are then more particularly interested in the luminous intensity in the case of photometry and in the amplitude of the various components of the polarised light in the case of ellipsometry.

We know, in particular, phase-modulated ellipsometry in which a modulator acts on the polarisation state of the incident luminous beam, the spectroscopic ellipsometry in which the wavelength spectrum of the reflected light is analysed and the modulated reflectometry that takes into account the effect of the modulation generated by a periodic external excitation, for example electric or optic excitation, acting on the sample. A modulated spectroscopic ellipsometer is for instance described in the European patent EP-0.663.590 to which reference can be made.

Each one of these major alternatives of optical characterising of a sample exhibits its own advantages.

Generally speaking, macroscopic response of a thin layered material to an electromagnetic excitation by a tensor $\epsilon(\omega)$ where $\omega$ is the frequency of the electromagnetic excitation. In the case of an isotropic solid, this tensor $\epsilon(\omega)$ is reduced to a scalar and we obtain the relationship $D=\epsilon_o \epsilon E$ where $\epsilon_o$ is electric permittivity of vacuum, D is the electric displacement vector and E is the applied electric field.

Polarisability $\alpha$ is then defined on the base of the local bipolar moment p (per atom or group of atoms). Indeed, p is linked with the local electric field $E_{loc}$ (itself function of the external electric field E by the relationship: $p=\alpha\epsilon_o E_{loc}$.

The macroscopic dipolar moment per volume unit or polarisation vector is given by the formula: $P=Np$ where N represents the space density of dipoles. Polarisation is linked with the other macroscopic quantities by the relation: $P=\epsilon_o (\epsilon-1) E$.

Reflectometry, more particularly, spectroscopic ellipsometry, enables accessing the dielectric function $\epsilon(\omega)$. In the range of wavelengths from ultraviolet to the visible, absorption is often dominated by electronic transitions (it is for example the case in semiconductors). In the infrared range, ellipsometry is sensitive to vibration absorption, i.e. dipole excitation. The thickness probed may vary considerably in relation to the wavelength as in the case of semiconductors that are generally very absorbing in the ultraviolet and quasi transparent in the infrared.

The Raman diffusion is, for its own part, sensitive to polarisability variations in the presence of excitations $\Delta\alpha(\omega)$.

It can be noted that, as regards the determination of related physical values, ellipsometry and Raman diffusion are techniques of different natures. In particular, from the viewpoint of quantum mechanics, the efficient sections of certain vibrations could be very different in one case and in the other.

Reflectometric measurement is conducted in a specular and elastic fashion (conservation of the wavelength), generally in reflection. Consequently, it is sensitive to interference phenomena that enable measuring thicknesses of thin layers. More generally, ellipsometry is well suited for characterising a multilayer material (which exhibits thickness divergences). In usual applications of ellipsometry, the angle of incidence varies between 55 and 80° approximately, which corresponds to the Brewster angles of most materials and provides optimal sensitivity. Two wavelength ranges are used generally: the first is said 'visible ultraviolet', extending from the near ultraviolet (0.25 $\mu$m) to the near infrared IR (1.7 $\mu$m) and the second, called 'infrared', in the more remote infrared from 2.5 to 12 or 16 $\mu$m approximately. Measurements with higher wavelengths are difficult because of experimental limits imposed by the sources and the detectors.

$\epsilon(\omega)$ is represented by a complex number whose determination calls generally for the measurement of two independent parameters as this can be made in ellipsometry. However, photometry, pending the use of so-called Kramers-Konig relationships, can also enable measuring $\epsilon(\omega)$. Modulated reflectometry techniques measure the variation of $\epsilon(\omega)$ in the presence of an external excitation, which brings complementary information. In particular, in semiconducting materials, the modulated external excitation generates loaded carriers that concur to that measurement.

Conversely, the Raman diffusion is inelastic. The measurement is then generally conducted in normal incidence; whereas a laser that emits a ray in the ultraviolet, the visible or the near infrared range provides the excitation. The Raman photons are collected under a solid wide angle at wavelengths close to those of the incident light. We therefore measure spectroscopically a positive or negative difference in wavelengths between the exciting ray and the Raman spectrum. By comparison, the remote reflectometry infrared corresponds in Raman to the wavelengths closest to the exciting wavelength. Such measurements are therefore technically easier in Raman spectrometry. It should be underlined that the characterised thickness is linked with the absorption of the material at the wavelength of the incident light that is hardly modifiable in Raman for a given material.

Thin films have been subject to Raman spectroscopy surveys as of the end of the sixties. It has been suggested first of all to study thin layers deposited on a metal surface. Lit under an angle of incidence of 70°, the Raman flux obtained exhibited a maximum intensity around 60°. It has then been proposed to use a thin layer as an optic wave-guide to which a light flux was coupled by means of a prism or of a grating. Under strict conditions of angle of incidence and of polarisation, one or several electric or magnetic transverse modes can be propagated in the film while creating therein a Raman flux whose intensity can reach up to two thousand times the flux intensity usually generated by backscattering.

In such a case, the minimum thickness of the film, linked with the excitation wavelength, cannot be smaller than a few nanometres. We can go below this limit only while resorting to multilayer structures. Anyway, all these methods call for particular preparation of the film or of the thin layer, on a specific support, which implies tooling and adjustments incompatible with the survey of industrial materials and even more with in situ or real-time measurements, during the implementation of a method of manufacture.

These presentations of the measurements by Raman effect on the one hand, and by reflectometry on the other hand, ellipsometric or photometric reflectometry, as they outline that we obtain different effects, hence different sources of knowledge and characterising, also show the difficulties that may be encountered especially when the material is thinly layered.

The realisation of the measurements on the same sample, by reflectometry and by Raman spectroscopy, exhibits other difficulties. Indeed, the different angles of incidence for one or the other of these measurements, the wavelengths also different call for optic apparatuses that are especially suited to each of the techniques and do not allow using the same source for lighting nor the same wavelength detection system for reception, in one and the other case.

Moreover, it has been considered for a long time that simultaneous implementation of both these techniques was liable to produce parasitic effects damaging the quality of each measurement. Thus, the backscattering Raman spectrometry measurements imply to light the sample with luminous intensities that can modify the sample while inducing annealed, crystallised or effused (extraction of hydrogen atoms for example) matters and risk to compromise reflectometric measurement.

It should be noted especially that the sizes of the zones lit by the sample during either of these measurements could be quite different.

Using a single type of measurement is for instance described in the document WO-97/05473, which relates to optic microsamples and methods for spectral analysis of materials. In a particular embodiment, a multimode optic fiber cuts a light source and a sample. The sample is also coupled to a sensor, which senses the light reflected by the sample lit, according to an angle predetermined with respect to the direction of the light.

Still, as regards the realisation of the Raman and reflectometric measurements on zones superimposed with a thin layer, simultaneously, exhibits great advantages, on the one hand directly as regards characterising materials, on the other as regards checking preparation methods that may implement such characterising modes. As measurements can be made simultaneously in real time, it is possible to follow the variations and the evolution relative to the velocity of the parameters measured. We obtain thus a very detailed physicochemical description of the layers, as it is illustrated below.

The aim of this invention is therefore to solve the various difficulties mentioned above and to suggest an apparatus that enables characterising a thin layer by backscattering Raman effect, without any risk of modifying the layer during measurement.

It is another aim of the invention to suggest an apparatus enabling simultaneous characterising by Raman effect and by reflectometry.

Reflectometry encompasses, as we have stated above, photometric measurements in which only the luminous energy is measured and the ellipsometric measurements in which the different polarised components of the light flux are considered. In both cases, reflectometry can be spectroscopic, i.e. spectral analysis of the measured flux is realised.

To this end, the invention concerns an apparatus for characterising a thin-layer material by backscattering Raman spectrometry comprising a frame, a monochromatic excitation laser source, optical means directing a light flux toward the material to be characterised, and means for collecting and selecting the light diffused by Raman effect.

In optical means directing the excitation laser flux toward the sample, there exists between the laser and the sample a means homogenising the distribution of energy per surface unit, over a minimum surface of some tens of square micrometers.

According to the invention, the apparatus comprises means for reflectometric measurement, integral with the Raman measuring means, whereas this reflectometric measuring means comprises reflectometric excitation means directed on the same zone of the sample as the Raman excitation means.

The apparatus of the invention can thus be used;
either for pure Raman spectrometry measurements,
or for pure reflectometric measurements,
or for combined Raman spectrometry and reflectometric measurements.

In different particular embodiments, each exhibiting their own advantages and liable to be implemented in numerous technically possible combinations:

the reflectometric measuring means are photometric measuring means;

the reflectometric measuring means are ellipsometric measuring means;

the means homogenising the distribution of energy comprises a multimode fiber;

the diameter of the fiber is suited to the surface of the sample that must be lit;

the fiber is interchangeable; thus the diameter lit can be changed using barrels with fibers of different diameters;

the apparatus comprises several barrels enabling to light the sample over a focusable zone over the slot of a spectrometer or to suit the Raman excitation surface to the surface analysed by photometry;

the reflectometric measuring means are modulated reflectometry measuring means;

the modulation is optical;

the modulation is electric;

the modulation is ensured by the Raman excitation source;

the reflectometric source is coupled to the remainder of the apparatus by an optical fiber;

at least one of the Raman and reflectometric receivers is connected to the remainder of the apparatus by an optical fiber.

The invention will be described in detail with reference to the appended Figures on which:

Figure 1:
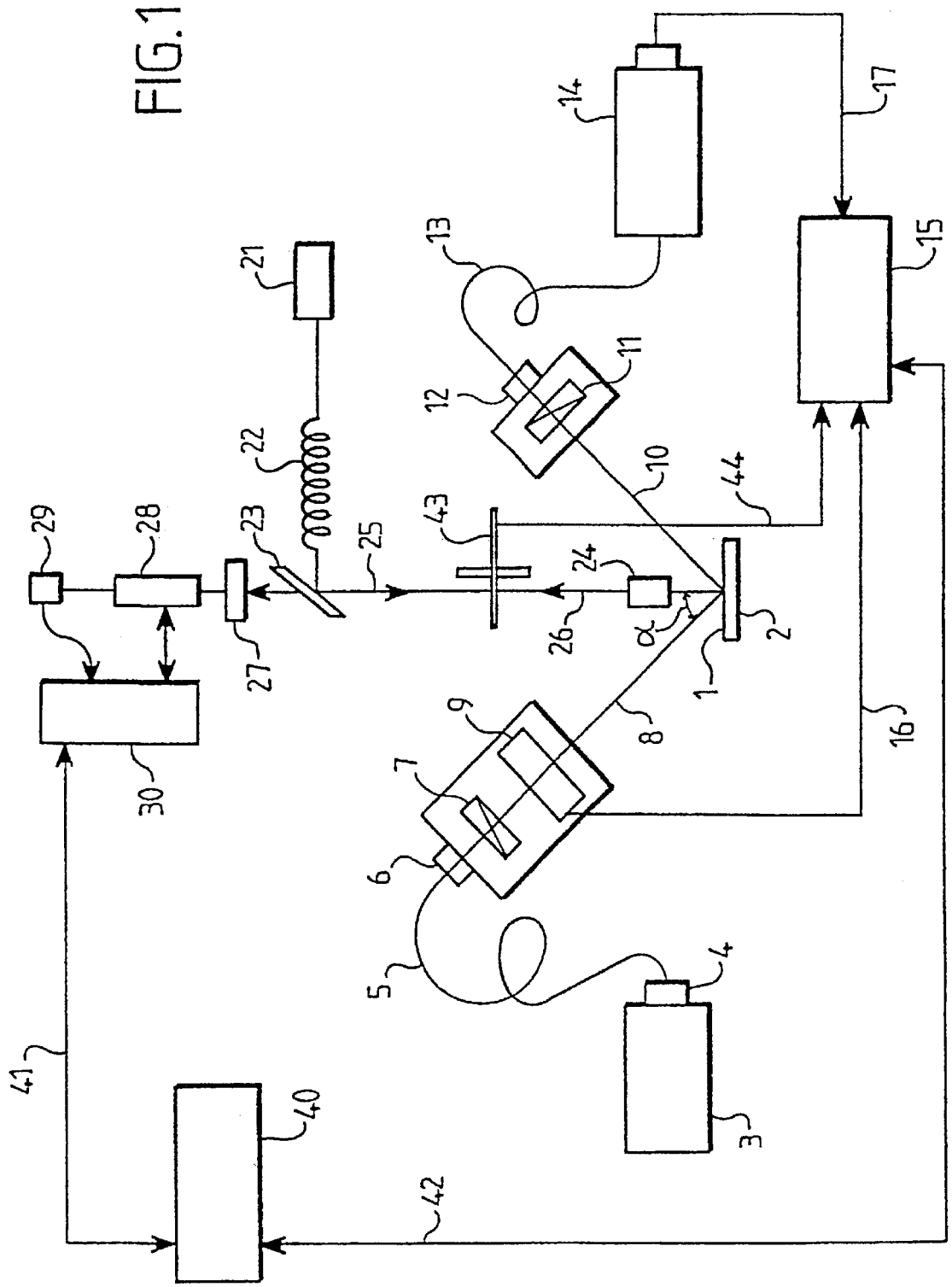
FIG. 1 is a principle diagram of the apparatus according to the invention.

The apparatus of the invention enables realising a Raman measurement at the point 1 of the sample 2. To this end, a light source 21 generates a light beam at a Raman excitation wavelength $\lambda_e$ emitted by a multimode fiber 22. This light beam is reflected by a blade 23 that directs it toward a lens 24 that focuses the said beam at the point 1 of the sample. A portion of the backscattered beam 26 by Raman effect is at a wavelength $\lambda_r$. A filter 27 enables selecting this Raman flux at the wavelength $\lambda_r$ and rejecting the flux diffused at the exciting wavelength $\lambda_e$. Thus, the beam emitted by the filter 27 does not contain any components at the excitation wavelength $\lambda_e$. This flux is analysed by a spectrometer 28 coupled with a sensor 29. A control unit 30 operates the spectrometer 28 and receives the information generated by the sensor 29.

In an intrinsically conventional fashion, the control unit 30, by processing the control information of the spectrometer 28 and the information supplied by the sensor 29, enables preparing Raman characterising data of the sample 2.

It has been noticed that the use of such a multimode fiber 22 modifies significantly the transverse distribution of the light energy contained in the flux coming from the source 21.

It is well known that this light distribution, at the output of the source 21 that is generally a laser, is Gaussian in its shape. This exhibits a difficulty for backscattering Raman spectroscopy if we want to light a relatively large surface of the sample. Focusing a Gaussian beam with a microscope lens produces a light spot whose diameter is close to the diffraction limit, i.e. 1.2 $\lambda$/na, whereas $\lambda$ is the wavelength and na the digital opening of the lens, i.e. in the visible with a lens na=0.9 and $\lambda$=0.5 $\mu$m a submicronic spot, hence a very high intensity per surface unit that damages or destroys the sample when it is a thin layer.

To remedy this shortcoming, it has been contemplated to preserve the power, but to defocus the beam at the sample. Thus, the transverse distribution of energy is enhanced, but it is not always homogeneous and shows apexes and valleys that raise the same adaptation problems as those mentioned above with a Gaussian beam.

This is for example analysed in the book by Born Wolf 'Principles of Optics' Perganon Press—NY 1993. The practical result is that defocusing a Gaussian beam by spherical, cylindrical or aspherical optics, is divergent and the modification of the layer does not take place in the centre automatically any longer, but the layer may still be destroyed or altered locally.

To remedy these shortcomings and to preserve the integrity of the thin layer studied, a multimode optical fiber is interposed between the monochromatic source and the layer. The interposition of this multimode optical fiber enables, while destroying the Gaussian distribution of energy, obtaining at the output of the said fiber homogeneous distribution of energy density that is approximately the same at the centre and on the edges of the lighting luminous spot.

Figure 2B:
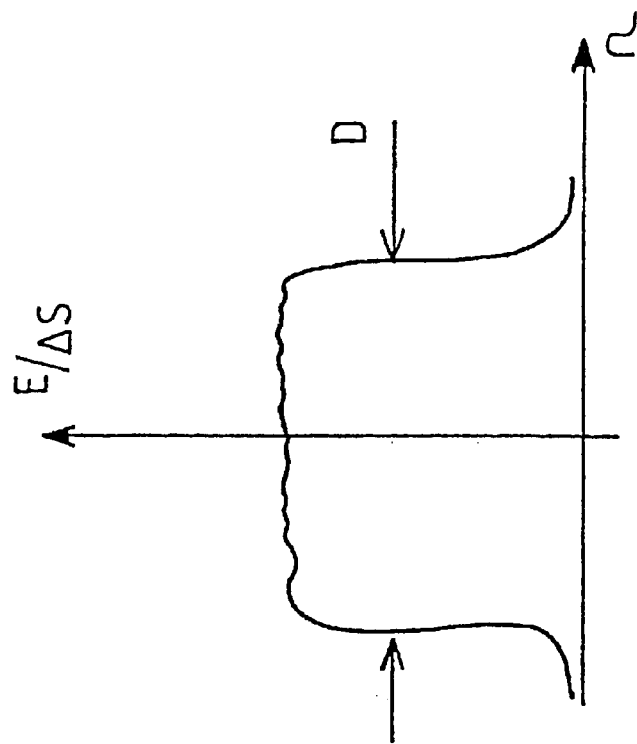
FIG. 2 is a diagrammatical representation of the transverse distribution of energy in a monochromatic light flux, on the one hand with a Gaussian beam (a), on the other hand after modification by the multimode optical fiber according to the invention (b).
Figure 2A:
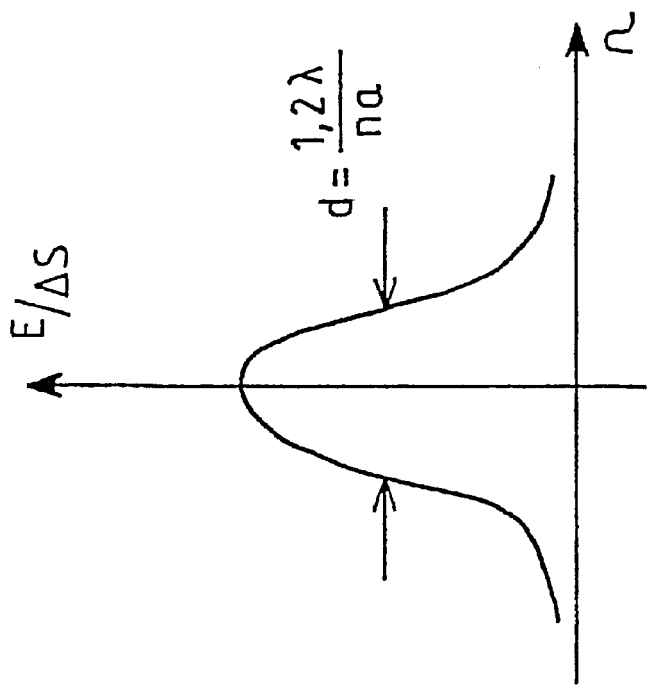

FIG. 2 gives a compared distribution of this light energy density E/ΔS via the beam, respectively for a Gaussian beam as it comes out of the laser (FIG. 2a) and of the same beam at the output of a multimode fiber (FIG. 2b).

The multimode optical fiber has preferably a diameter D in the order of 100 microns and a length of at least a few delimiters.

In Raman microscopy, with an ×50 lens, we obtain an excitation of the sample on a disk of this diameter D of approximately 20 microns.

We obtain then an energy density on this sample in the order of 3.3 Watts/mm$^2$ for a laser with a power in the order of one milliwatt.

While changing the diameter of the optical fiber, the energy density can be modified.

It is also possible to excite the energy with several fibers, whereas the excitation points are distributed along a line, the flux collected is focused on the input slot of the analysis spectrometer.

The idea is to characterise the zone 1 of the sample 2. This characterising is conducted on the one hand by ellipsometry. An ellipsometric source 3 is connected by a coupler 4 to an optical fiber 5 that carries the light flux produced by the source and directs it via a coupler 6 to a polarizer that generates a light beam 8 sent onto the sample 1 under an angle of incidence $\alpha$.

Between the polarizer 7 and the sample is arranged a phase modulator 9 that performs, in a known fashion, modulation of the polarisation state of the light beam 8.

The beam 8 is reflected by the sample 2 into a light beam 10 that is analysed by a polarizer 11 and coupled by an optical system 12 with a fiber 13 that it directs to a photo-receiver 14 that may comprise a wavelength-related selection facility. A control unit 15 operates the phase modulator 9 and via the connection 16. This control unit 15 receives the signal generated by the photo-receiver 14 via the line 17.

By processing this data, the control unit 15 is capable of supplying the ellipsometric information significant of the sample 2 and liable to enable its ellipsometric characterising.

The ellipsometric control units on the one hand and the Raman control units 30 on the other are connected electrically to a global control computer 40 that is the interface using the whole apparatus and enables complete physicochemical characterising of the point 1 of the sample 2.

The ellipsometric measuring means described above implement a phase-modulation ellipsometer, the device of the invention can operate with any type of ellipsometer, spectroscopic or not, and even with photometers that analyse the reflected flux 10 independently of its polarisation state, but generally in relation of the wavelength. A phase-modulation ellipsometer enables simultaneous photometric and ellipsometric measurements.

The ellipsometric means incorporate advantageously external modulation means generating electric, optical or thermal effects on the sample at a determined frequency. These means can be for example a revolving screen or shutter 43 whose orientation determining the modulation frequency and phase is operated by the control unit 15 via the line 44.

Advantageously, Raman excitation means, i.e. the light beam 25 generated by the Raman excitation source 21, constitutes the ellipsometric modulation means.

The zone of the sample measured during the Raman measurement is positioned accurately and preferably ranging in that provided by the ellipsometric measurement. Both these measurements can be made simultaneously.

The apparatus of the invention is particularly suited to the following applications in which it enables realisation of characterising operations that had been difficult so far:

a) Thin-layered Polycrystalline (or Microcrystalline) Silicium

Partially crystallised silicium is used very currently in the semiconductor industry. It consists of crystallites of variable sizes linked with amorphous gain joints.

This material is often divergent in thickness and exhibits in particular a surface roughness linked with the size of the crystallites. The ellipsometry in the field of wavelength extending from the ultraviolet to the visible enables very accurate ($\approx$1%) of the total thickness and of the roughness ($\leq$50 nm), that are very hardly accessible in Raman. Generally speaking, the UV-visible ellipsometry is far more sensitive to the morphology of the layers (density, . . . ).

Both techniques enable measurement of the mean composition (crystalline fraction) of the layer, whereas the ellipsometry enables characterising any thickness divergence.

Conversely, the size of the grains can be determined by Raman spectrometry, whereas it is very hardly measurable by reflectometry. Similarly, Raman spectrometry enables assessing the existing stresses within the material on the basis of the displacement of the wavelength of the characteristic rays. These stresses are almost inaccessible by reflectometry, for example by ellipsometry.

Ellipsometry characterising (mainly here in the UV-visible range) and Raman characterising are therefore complementary.

b) Thin-layered Carbon

The thin carbon layers are used in many applications. The considerations developed in relation to the previous example, in terms of thickness and morphology (density, roughness) apply obviously in the case of thin-layered carbon as well.

Carbon may be crystalline or amorphous. Two crystalline forms exist in nature: diamond (hybridisation $sp^3$) or graphite (hybridisation $sp^2$) with very different properties. It is possible to identify them by Raman spectrometry and by ellipsometry as well.

In amorphous form, both phases generally coexist, influencing considerably the practical properties (hardness, . . . ), whereas 'adamantine' carbon is for example rich in phase $sp^3$. However, both these phases often appear linked with one another at atomic scale, without it being possible to identify aggregates as in the previous case. These thin layers, often deposited by plasma, contain an important proportion of hydrogen, which may also influence the properties (whereby the layers may even appear as polymeric).

$CH_n$ vibrations are more easily identifiable by Infrared ellipsometry than by Raman spectrometry because of the differences in efficient sections. Still, generally, hydrogen is essentially integrated into the phase $sp^3$. IR ellipsometry is therefore well suited to characterising the phase $sp^3$. As in the previous example, the apparatus of the invention that enables measurements in real-time and at the same point, by Raman spectrometry and by reflectometry, ensures complete characterising such samples.

c) Polymers

In the case of polymers, complementarity of IR ellipsometry and Raman spectrometry is due to the various sensitivities of both techniques at diverse vibrations, whereas Raman spectrometry is very sensitive to C=C groupings, and IR ellipsometry to C=O groupings present in numerous polymers such as polycarbonate. The apparatus of the invention enabling implementation of both these types of measurement at the same time and at the same point allows taking full advantage of this complementarity. Generally speaking, Raman spectrometry is complementary to remote IR ellipsometry while allowing for benzenic core deformation-sensitive characterising.

Certain polymer processes illustrate complementarity of Raman spectrometry and of UV-visible ellipsometry further, for example by plasma. A cross-linking phenomenon will be put in evidence readily, by ellipsometry, by means of an increased refraction index (densification) or of an absorption in the UV (emergence of chromophor groupings) range. In an analogue fashion, we could put a degradation process in evidence. The polymer thickness, concerned by modification, will be assessed in ellipsometry thanks to multilayer formalism. Conversely, UV-visible ellipsometry, little sensitive to the structure of the material, will be ill suited for describing the cross linking or degradation microscopic mechanism. The structure modification of the polymer or a polymerisation state could be characterised easily by Raman spectrometry measurements.

These embodiments of the apparatus of the invention illustrate its benefit and are not limiting in any way.

What is claimed is:

1. An apparatus for characterising a thin-layer material by backscattering Raman spectrometry comprising a frame, a monochromatic excitation laser source (21), optical means (23, 24) directing a light flux that is emitted by the excitation source (21) toward the material to be characterised, and means for collecting (24) and selecting (27, 28) the light diffused by Raman effect, whereas the said apparatus is such that in the optical means directing the excitation laser flux toward the material, there exists between the laser and the material a means (22) homogenising the distribution of energy per surface unit, over a minimum surface of some tens of square micrometers, characterised in that the said apparatus comprises means for reflectometric measurement (3–14), integral with the collecting and selecting means, whereas this reflectometric measuring means comprises reflectometric excitation means (3–9) directed on the same zone of the material as the Raman excitation means.

2. An apparatus for characterising a thin-layer material according to claim 1, characterised in that the reflectometric measuring means are photometric measuring means.

3. An apparatus for characterising a thin-layer material according to claim 1, characterised in that the reflectometric measuring means are ellipsometric measuring means.

4. An apparatus for characterizing a thin-layer material according to any of claims 1 to 3, characterized in that the said means homogenising the distribution of energy comprises a multimode fiber (22).

5. An apparatus for characterizing a thin-layer material according to claim 4, characterizing in that the diameter of the fiber (22) is suited to the surface of the sample that must be lit.

6. An apparatus for characterising a thin-layer material according to claim 4, characterised in that the fiber (22) is interchangeable.

7. An apparatus for characterising a thin-layer material according to claim 4, characterised in that it comprises several fibers enabling to light the sample over a focusable zone over the slot of a spectrometer or to suit the Raman excitation surface to the surface analysed by photometry.

8. An apparatus for characterising a thin-layer material according to any of claims 1 to 3, characterised in that the reflectometric measuring means are modulated reflectometry measuring means.

9. An apparatus for characterising a thin-layer material according to claim 8, characterised in that the modulation is optical.

10. An apparatus for characterising a thin-layer material according to claim 8, characterised in that the modulation is electric.

11. An apparatus for characterising a thin-layer material according to claim 9, characterised in that the modulation is ensured by the Raman excitation source.

12. An apparatus for characterising a thin-layer material according to any of claims 1 to 3, wherein the reflectometric excitation means comprises an optical fiber coupled to a reflectometric source.

13. An apparatus for characterising a thin-layer material according to any of claims 1 to 3, wherein the reflectometric measuring means comprises a reflectometric receiver, and wherein at least one of the collecting and selecting means and reflectometric receivers is connected by an optical fiber.

* * * * *